(12) United States Patent
Lemieux et al.

(10) Patent No.: US 9,195,044 B2
(45) Date of Patent: Nov. 24, 2015

(54) OPTICAL PROBE HAVING AN INNER TUBE WITH SEPARABLE TUBE SECTIONS TO HOUSE OPTICAL ELEMENTS

(71) Applicants: Dennis H. Lemieux, Casselberry, FL (US); David W. Fox, Chuluota, FL (US); James P. Williams, Orlando, FL (US)

(72) Inventors: Dennis H. Lemieux, Casselberry, FL (US); David W. Fox, Chuluota, FL (US); James P. Williams, Orlando, FL (US)

(73) Assignee: SIEMENS ENERGY, INC, Orlando, FL (US)

( * ) Notice: Subject to any disclaimer, the term of this patent is extended or adjusted under 35 U.S.C. 154(b) by 45 days.

(21) Appl. No.: 14/077,254

(22) Filed: Nov. 12, 2013

(65) Prior Publication Data

US 2015/0049396 A1 Feb. 19, 2015

Related U.S. Application Data

(60) Provisional application No. 61/866,206, filed on Aug. 15, 2013.

(51) Int. Cl.
*G02B 7/02* (2006.01)
*G02B 23/24* (2006.01)
*A61B 1/00* (2006.01)

(52) U.S. Cl.
CPC ........ *G02B 23/2492* (2013.01); *A61B 1/00096* (2013.01); *G02B 23/2423* (2013.01); *G02B 23/2446* (2013.01); *G02B 23/2476* (2013.01)

(58) Field of Classification Search
CPC ............. A61B 1/0011; A61B 1/00096; A61B 1/00177; A61B 1/00128; A61B 1/00183; A61B 2562/0233; A61B 1/042; G01N 21/8507; G01N 21/954
See application file for complete search history.

(56) References Cited

U.S. PATENT DOCUMENTS

| | | | |
|---|---|---|---|
| 4,934,137 A | 6/1990 | MacKay | |
| 5,112,127 A | 5/1992 | Carrabba et al. | |
| 5,463,712 A | 10/1995 | Cawood | |
| 5,586,977 A | 12/1996 | Dorsey, III | |
| 7,231,817 B2 | 6/2007 | Smed et al. | |
| 7,294,817 B2 | 11/2007 | Voigt et al. | |
| 7,489,811 B2 | 2/2009 | Brummel et al. | |
| 7,690,840 B2 | 4/2010 | Zombo et al. | |
| 8,063,372 B2 | 11/2011 | Lemieux et al. | |
| 8,184,151 B2 | 5/2012 | Zombo et al. | |
| 8,413,493 B1 | 4/2013 | Polywoda, III | |
| 8,439,630 B2 | 5/2013 | Lemieux et al. | |
| 2004/0101023 A1 | 5/2004 | Choi | |
| 2006/0088793 A1 | 4/2006 | Brummel et al. | |
| 2007/0107504 A1 | 5/2007 | Smed et al. | |
| 2011/0069165 A1 | 3/2011 | Zombo et al. | |
| 2012/0098940 A1 | 4/2012 | Zombo et al. | |
| 2012/0162192 A1 | 6/2012 | Wang et al. | |
| 2012/0194667 A1 | 8/2012 | Banerjee et al. | |
| 2012/0281084 A1 | 11/2012 | Hatcher et al. | |
| 2013/0038872 A1 | 2/2013 | Fujiwara et al. | |
| 2013/0194413 A1* | 8/2013 | Hatcher et al. | 348/82 |

* cited by examiner

*Primary Examiner* — Alicia M Harrington

(57) ABSTRACT

An optical probe (10) including one or more optical elements (32), and an inner tube (30) to house the optical elements. The inner tube may be made up of at least two cooperating inner tube sections (34, 36) separable from one another along a longitudinal axis of the inner tube.

14 Claims, 6 Drawing Sheets

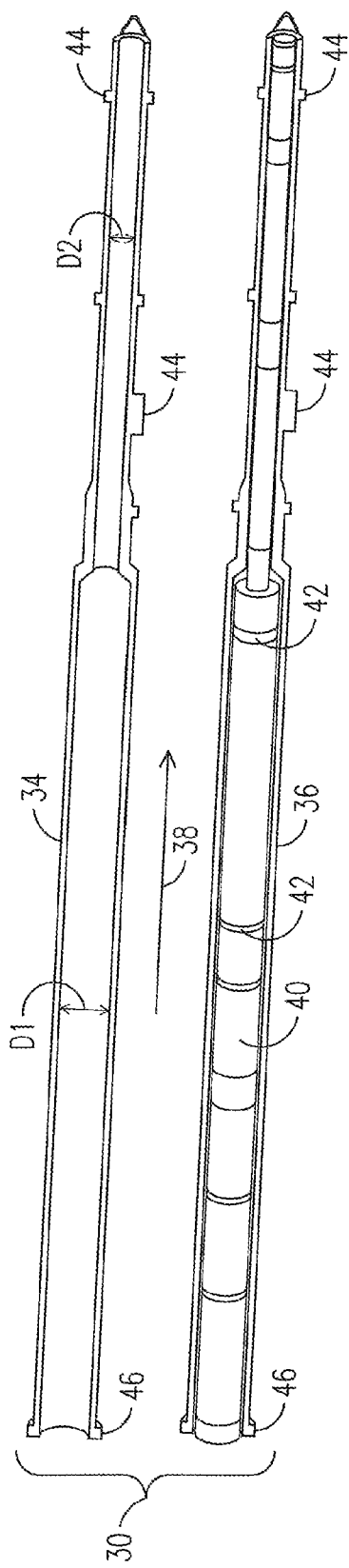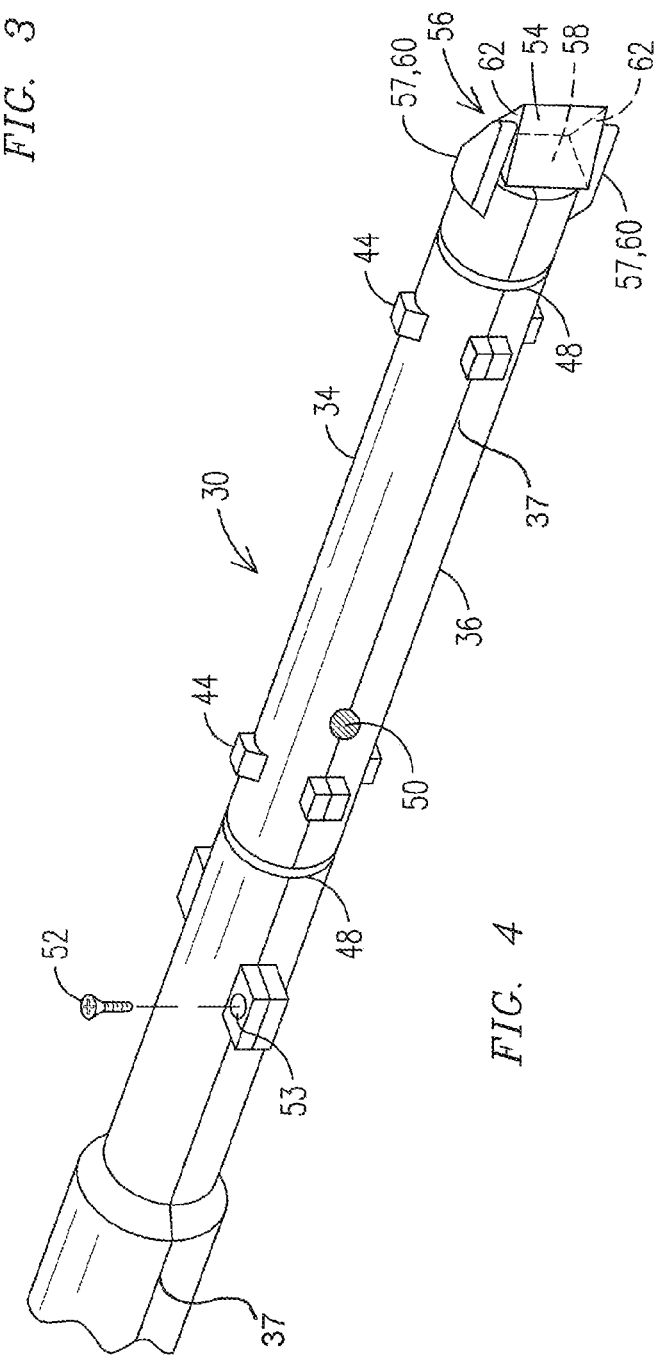

OPTICAL PROBE HAVING AN INNER TUBE WITH SEPARABLE TUBE SECTIONS TO HOUSE OPTICAL ELEMENTS

This application claims benefit of the 15 Aug. 2013 filing date of United States Provisional Patent Application No. 61/866,206, which is incorporated by reference herein.

FIELD OF THE INVENTION

The invention is generally directed to monitoring of turbine engines, and, more particularly, to an optical probe for optical monitoring of turbine engines.

BACKGROUND OF THE INVENTION

Notwithstanding of advances which have been made in this technical field, there continues to be a need for improved apparatus and/or techniques useful for monitoring high-temperature regions of interest in a turbine engine.

BRIEF DESCRIPTION OF THE DRAWINGS

The invention is explained in the following description in view of the drawings that show:

FIG. 3 is an isometric view of an inner tube of an optical probe embodying aspects of the present invention, where it can be appreciated that in one non-limiting embodiment, the inner tube may comprise at least two inner tube sections separable from one another along a longitudinal axis of the inner tube.

FIG. 4 is an isometric view where the inner tube sections of the inner tube are shown attached to one another, and further illustrates a light-redirecting element, (e.g., prism, mirrors) which may be supported at a distal end of the inner tube by an affixing structure embodying further aspects of the present invention.

DETAILED DESCRIPTION OF THE INVENTION

The present inventors have innovatively recognized that the serviceability of existing optical probes for monitoring components of combustion engines, e.g., turbine engines, may be substantially limited by the monolithic (e.g., single-piece) construction of structures that contain various optical elements which may be utilized by such optical probes to convey imaging data to an imaging sensor. In case of breakage of any of such optical components, gaining accessibility to replace or repair any such components is substantially burdensome, if at all feasible. The present inventors have further recognized that optical properties of certain optical elements (e.g., a prism) of existing optical probes may be impaired when such elements are attached by way of epoxies that may involve one or more optically-working surfaces of the prism.

In accordance with one or more embodiments of the present invention, structural arrangements and/or techniques conducive to an improved optical probe are described herein. For example, in lieu of a single-piece construction, in one non-limiting embodiment, such improved optical probes may provide an inner tube comprising at least two corresponding inner tube sections separable from one another along a longitudinal axis of the inner tube. In another non-limiting embodiment, such improved optical probes, may provide an affixing structure not attached to an optically-working surface of a light-redirecting element (e.g., prism, mirrors). In the following detailed description, various specific details are set forth in order to provide a thorough understanding of such embodiments. However, those skilled in the art will understand that embodiments of the present invention may be practiced without these specific details, that the present invention is not limited to the depicted embodiments, and that the present invention may be practiced in a variety of alternative embodiments. In other instances, methods, procedures, and components, which would be well-understood by one skilled in the art have not been described in detail to avoid unnecessary and burdensome explanation.

Furthermore, various operations may be described as multiple discrete steps performed in a manner that is helpful for understanding embodiments of the present invention. However, the order of description should not be construed as to imply that these operations need be performed in the order they are presented, nor that they are even order dependent unless otherwise so described. Moreover, repeated usage of the phrase "in one embodiment" does not necessarily refer to the same embodiment, although it may. Lastly, the terms "comprising", "including", "having", and the like, as used in the present application, are intended to be synonymous unless otherwise indicated.

Figure 1:
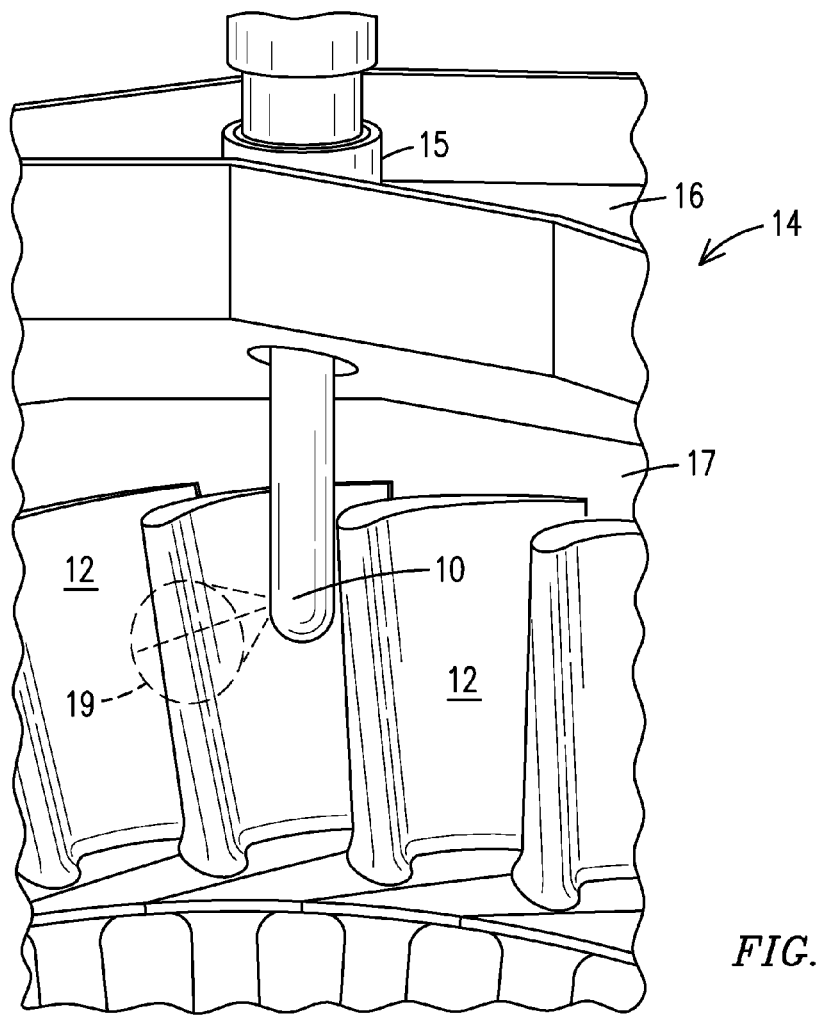
FIG. 1 is an isometric view of a non-limiting embodiment of an optical probe embodying aspects of the present invention, which may be used for optical monitoring of various components of a combustion engine, e.g., a turbine engine.

FIG. 1 is an isometric view of a non-limiting embodiment of an optical probe 10 embodying aspects of the present invention, which may be used for optical monitoring (e.g., inspection) of various components 12 (e.g., blades, vanes, etc.) of a combustion engine 14, e.g., a turbine engine. Optical probe 10 may be mounted through a viewing port 15 in a turbine casing 16 and may be partially disposed within a path 17 of hot-temperature working gases for the engine. Circle 19 is used to conceptualize one non-limiting example of a field of view which may be provided by optical probe 10.

Figure 2:
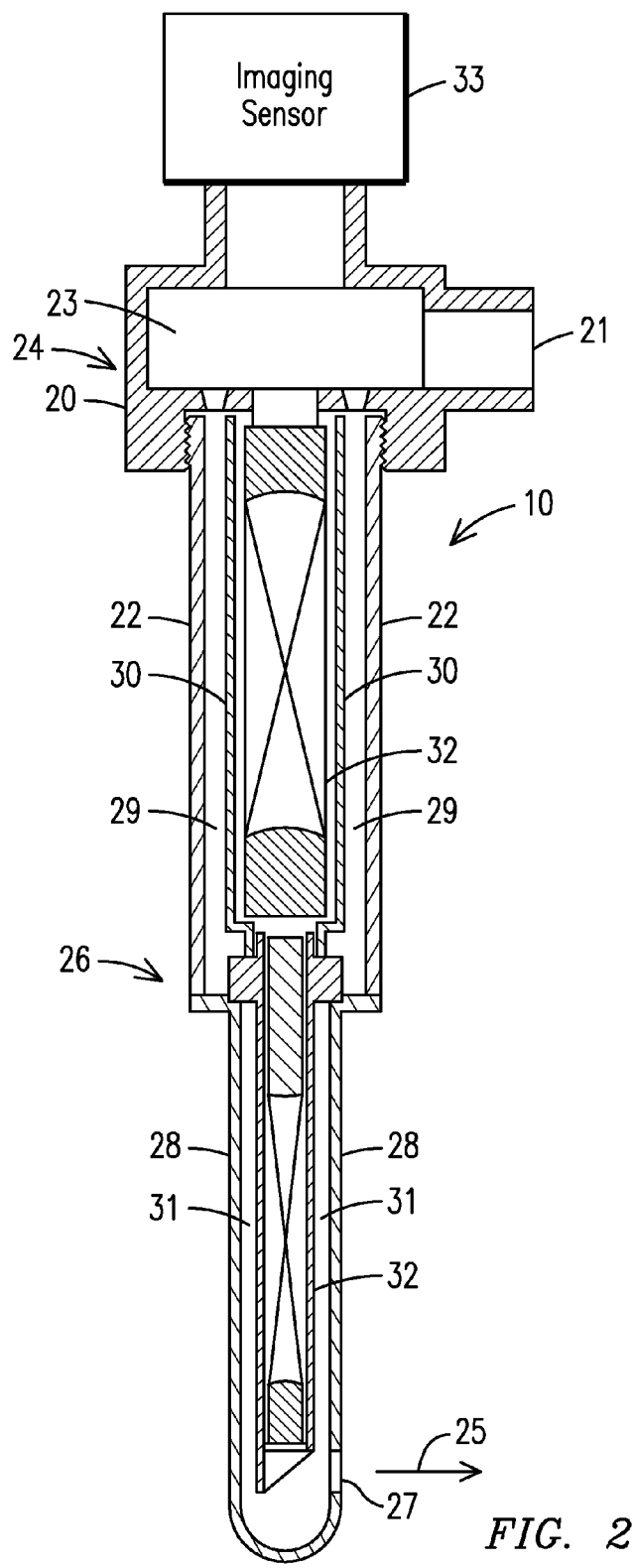
FIG. 2 is a generally cross-sectional view of one non-limiting embodiment of an optical probe embodying aspects of the present invention.

FIG. 2 is a generally cross-sectional view of one non-limiting embodiment of an optical probe 10 embodying aspects of the present invention. Probe 10 may comprise a fitting 20 including a port 21 and a plenum 23 for receiving a controllable supply of a cooling fluid, which in one non-limiting embodiment may be gaseous nitrogen (GN2). Probe 10 may further comprise an intermediate outer tubing 22 connected at a proximate end 24 to fitting 20 and at a distal end 26 to a probe tip 28, which may comprise a viewing window 27 and which may also define an opening for purging cooling fluid (schematically represented by arrow 25). Outer tubing 22 and probe tip 28 may be configured to receive in their respective hollowed interiors an inner tube 30, which may house at least one optical element (e.g., one or more optical lenses 32, which may be arranged as relay optics).

FIG. 2 further illustrates an imaging sensor 33, responsive to imaging data of one or more components of turbine engine disposed in the field of view of the probe and which imaging data may be conveyed to imaging sensor 33 by the relay optics. Imaging sensor 33 in one non-limiting embodiment may be an infrared (IR) camera (e.g., which may operate in the near-IR spectrum) or other suitable two-dimensional imaging sensing array. In one non-limiting embodiment, in lieu of optical lenses, optical fibers may be used to convey the imaging data to imaging sensor 33.

FIG. 3 is an isometric view of inner tube 30, where it can be appreciated that in one non-limiting embodiment inner tube 30 may comprise at least two corresponding and cooperating inner tube sections 34, 36 separable from one another along respective joint lines 37 (one of such joint lines is visible in FIG. 4) co-axially extending in a direction along a longitudinal axis 38 over an entire longitudinal length of the inner tube 30. FIG. 3 illustrates inner tube sections 34, 36 in a separated condition while FIG. 4 illustrates inner tube sections 34, 36 in a joined condition. That is, inner tube sections 34, 36 are illustrated in FIG. 4 as being attached to one another.

FIG. 3 further illustrates that one of the inner tube sections (e.g., inner tube section 36) may be filled with a series of optical lenses 40 (e.g., relay optics) stacked along the longitudinal axis 38 of inner tube 30. In one non-limiting embodiment, at least one optical spacer 42 may be interposed between at least a pair of the optical lenses. In one non-limiting embodiment, inner tube sections 34, 36 of inner tube 30 may define a hollowed interior having a varying diameter, as conceptually represented by the twin-headed arrows labeled D1 and D2, which in turn allows accommodating optical elements having a varying diameter. In one non-limiting embodiment, inner tube 30 may include at least one alignment tab 44 formed on an outer surface of inner tube 30. Inner tube 30 may further include a stop 46 formed on its outer surface. In one non-limiting embodiment, inner tube 30 may be configured to define respective annular spaces 29, 31 (FIG. 2) between its outer surface and the respective inner surfaces of outer tubing 22 and probe tip 28. These annular spaces allow externally-supplied cooling fluid to flow between such surfaces and this cooling arrangement is expected to avoid a need for relatively costly and rare high-temperature optical elements, which otherwise could be needed in order to withstand the relatively high temperatures encountered in a turbine engine environment. Moreover, such a cooling arrangement is expected to eliminate relatively large temperature fluctuations in the probe, which otherwise could produce optical aberrations, (e.g., focal point fluctuations) such as due to physical shifting of the optical elements and/or warping of structures therein. Although tube sections 34, 36 need not be attached to one another by way of hinges, tube sections 34, 36 may be conceptually analogized to a clam-shell structure for containing and effecting fast and uncomplicated retrieval (when needed) of any of the various optical elements contained in the interior of inner tube 30.

A means for removably affixing inner tube sections 34, 36 to one another may include one or more affixing elements. As illustrated in FIG. 4, non-limiting examples of affixing elements may include straps 48 (e.g., nickel-chromium alloy straps), tack-welds 50, threaded affixing elements 52 (e.g., screws, bolts and nuts), which for example may be inserted through respective openings 53 on corresponding alignment tabs, and a combination of two or more of such affixing elements.

Figure 5:
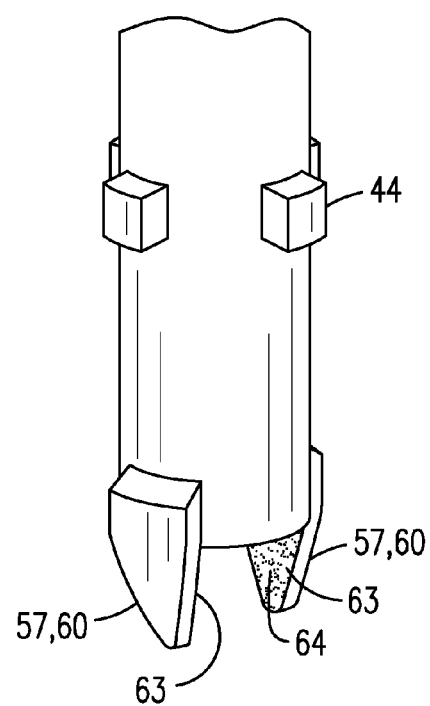
FIG. 5 is an isometric view illustrating further details in connection with the affixing structure illustrated in FIG. 4.

FIG. 4 further illustrates a light-redirecting element 54, which may be disposed at a distal end 56 of inner tube 30. In one non-limiting embodiment, light-redirecting element 54 may be a prism (e.g., a triangular prism), which may be supported at distal end 56 by an affixing structure 57 not attached to an optically-working surface 58 of light-redirecting element 54 (e.g., a back end of the prism). In one non-limiting example, affixing structure 57 may comprise one or more protrusions 60 from inner tube sections 34, 36 having a support surface 63 (FIG. 5) attached to a corresponding non-optically working surface of the light-redirecting element, such as lateral surfaces 62 (FIG. 4) of light-redirecting element 54. A layer 64 (FIG. 5) of adhesive may be disposed between support surface 63 and the corresponding surface of light-redirecting element 54 to establish a joining bond between such surfaces.

In one non-limiting embodiment, protrusions 60 may be integrally constructed (e.g., machined) at the respective distal ends of inner tube sections 34, 36 of inner tube 30. It will be appreciated that affixing structure 57 need not be integrally constructed with inner tube sections 34, 36 since, as will be now appreciated by one skilled in the art, affixing structure 57 in one alternative embodiment may be a separate structure, which is mountable onto the respective distal ends of inner tube sections 34, 36. It will be appreciated that alternative modalities for light-redirecting element 54 may include one or more reflecting surfaces (e.g., mirrors) arranged to redirect light.

Figure 6:
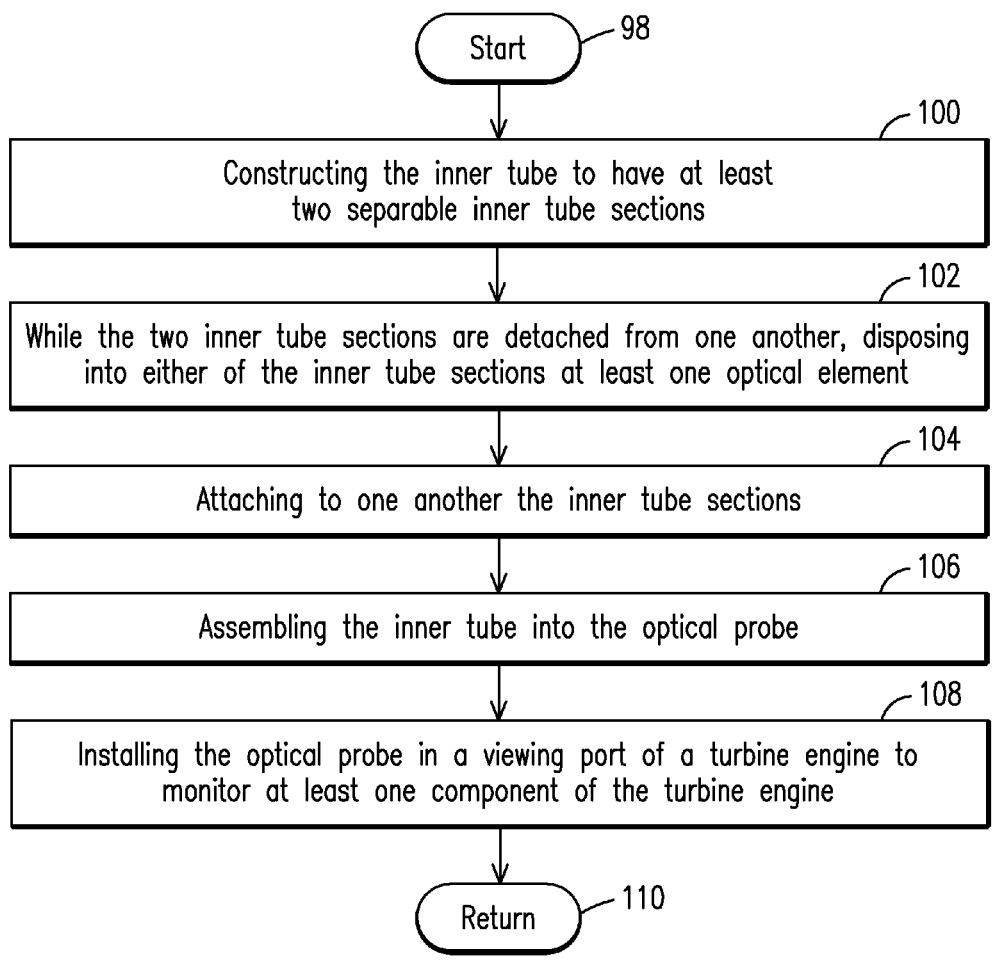
FIG. 6-8 each illustrates respective flow charts of non-limiting embodiments of methods that may be practiced in connection with optical probes disclosed herein for monitoring turbine engines.

An optical probe having separable inner tube sections configured to house at least one optical element, as disclosed above in the context of FIGS. 1-5, may be used to practice one or more methods, which in one non-limiting embodiment may be described below referring to the flow chart shown in FIG. 6.

Subsequent to a start step 98, step 100 allows constructing inner tube 30 (FIG. 3) to have at least two corresponding inner tube sections 34, 36 separable from one another along longitudinal axis 38 of the inner tube 30. While inner tube sections 34, 36 are detached from one another, step 102 allows disposing into either of inner tube sections 34, 36 at least one optical element, e.g., optical lenses 40, optical spacers 42, as shown in FIG. 3. As will be now appreciated by one skilled in the art, inner tube sections 34, 36 may be fully or partially separable (e.g., by way of hinge elements) from one another. Accordingly, the inner tube sections need not be fully detached from one another since partial separation of inner tube sections 34, 36 (e.g., analogous to an open clam shell) would provide practically unimpeded access to their respective interiors to install and/or or retrieve optical elements therein.

Step 104 allows attaching to one another corresponding inner tube sections 34, 36 by way of at least one removable affixing element, which without limitation may include as shown in FIG. 4, straps 48, weld tacks 50, threaded affixing elements 52. Inner tube 30 may then be assembled (step 106) with other components of optical probe 10, such as inserted into probe tip 28 and outer tubing 22, connected to fitting 20, etc., (see FIG. 2). Prior to a return step 110, optical probe 10 may then be installed (step 108) in viewing port 15 (FIG. 1) of turbine engine 14 to monitor at least one component (12) of the turbine engine. As may be appreciated in FIG. 1, at least a portion of optical probe 10 may be located in the hot-temperature environment of turbine engine 14.

Figure 7:
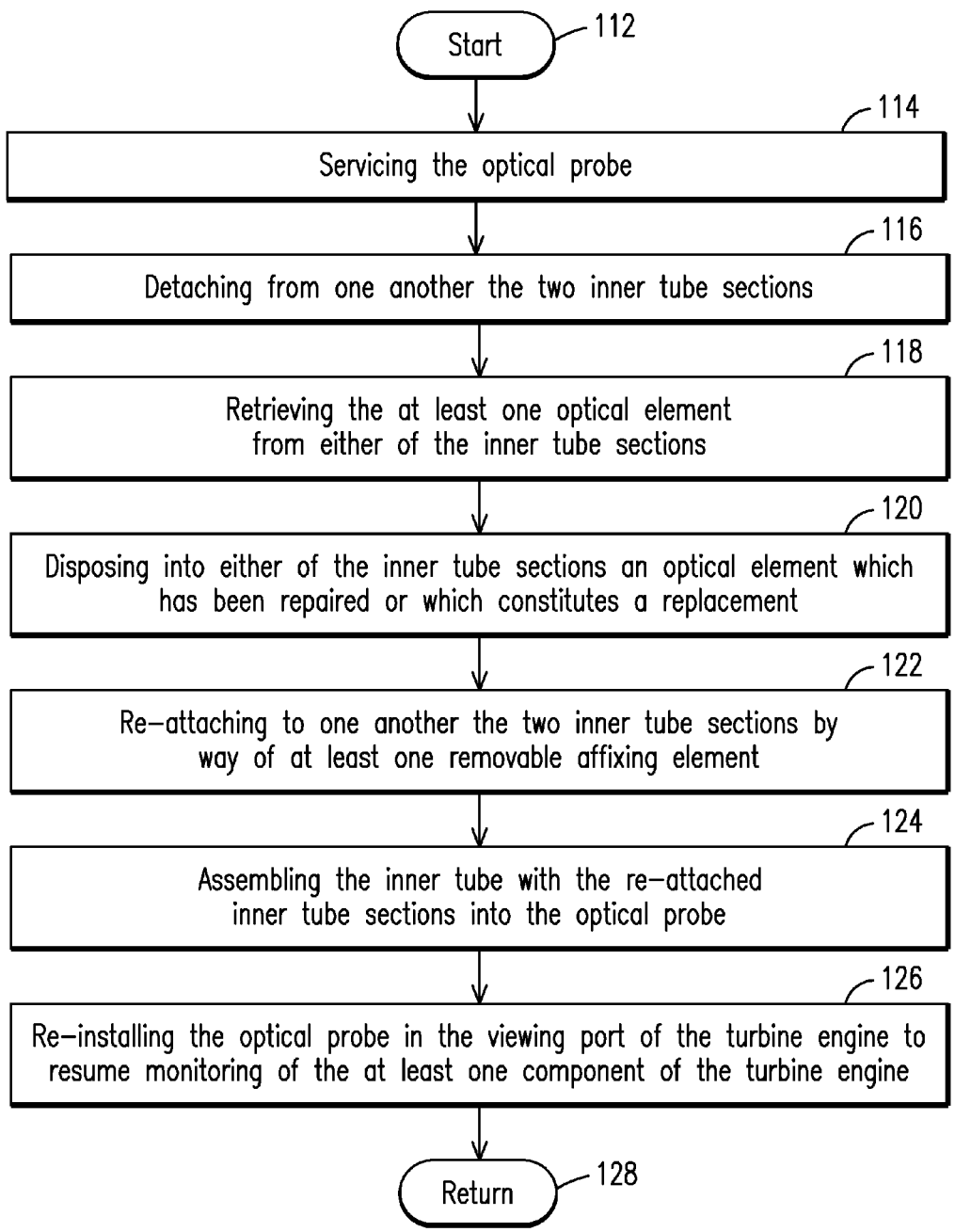

In one-limiting embodiment and referring to the flow chart shown in FIG. 7, in the event a servicing action (step 114) for optical probe 10 may be needed subsequent to a start step 112, optical probe 10 may be removed from viewing port 15 (FIG. 1) of turbine engine 14, and inner tube sections 34, 36 (FIG. 4) may be detached (step 116) from one another by removing the one or more affixing elements. This allows retrieving (step 118) the at least one optical element e.g., optical lenses 40, optical spacers 42, as shown in FIG. 3 from either of the inner tube sections to determine a servicing action to perform next regarding any such optical elements.

In one non-limiting embodiment, a servicing action may comprise replacing or repairing any such optical elements. Step 120 allows disposing into either of the inner tube sections 34, 36 at least one optical element which has been repaired or which constitutes a replacement for any retrieved optical element. Step 122 allows re-attaching to one another the two corresponding inner tube sections 34, 36 by way of at least one removable affixing element. Step 124 allows assembling the inner tube with the re-attached inner tube sections into the optical probe. Prior to a return step 128, step 126 allows re-installing optical probe 30 into viewing port 15 of turbine engine 14 to resume monitoring of the one or more components of the turbine engine.

The present inventors have further recognized that partitioning (e.g., cutting) a physical structure generally involves certain tangible loss of material. In the case of conventional symmetrical bifurcating of a tube (e.g., cutting intended to divide the tube into two equal size portions along the longitudinal axis of the tube), the loss of material can lead to geometrical distortions and/or fitting incompatibilities between the tubing sections resulting from such symmetrical bifurcating. Accordingly, the present inventors propose innovative asymmetrical bifurcating of two different tubing structures, which solves in an elegant and cost-effective manner the foregoing issues, and, for example, may be effective to snugly accommodate cylindrical-shaped optical elements in the interior of the tubing structures.

Figure 9:
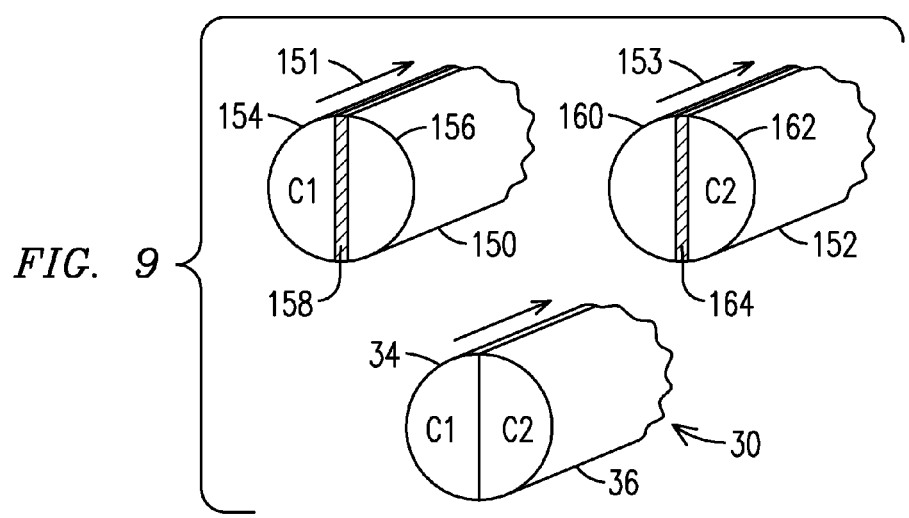
FIG. 9 shows respective isometric views of two separate tubing structures, which may be asymmetrically bifurcated to compensate for loss of material to construct an optical probe embodying aspects of the present invention.
Figure 8:
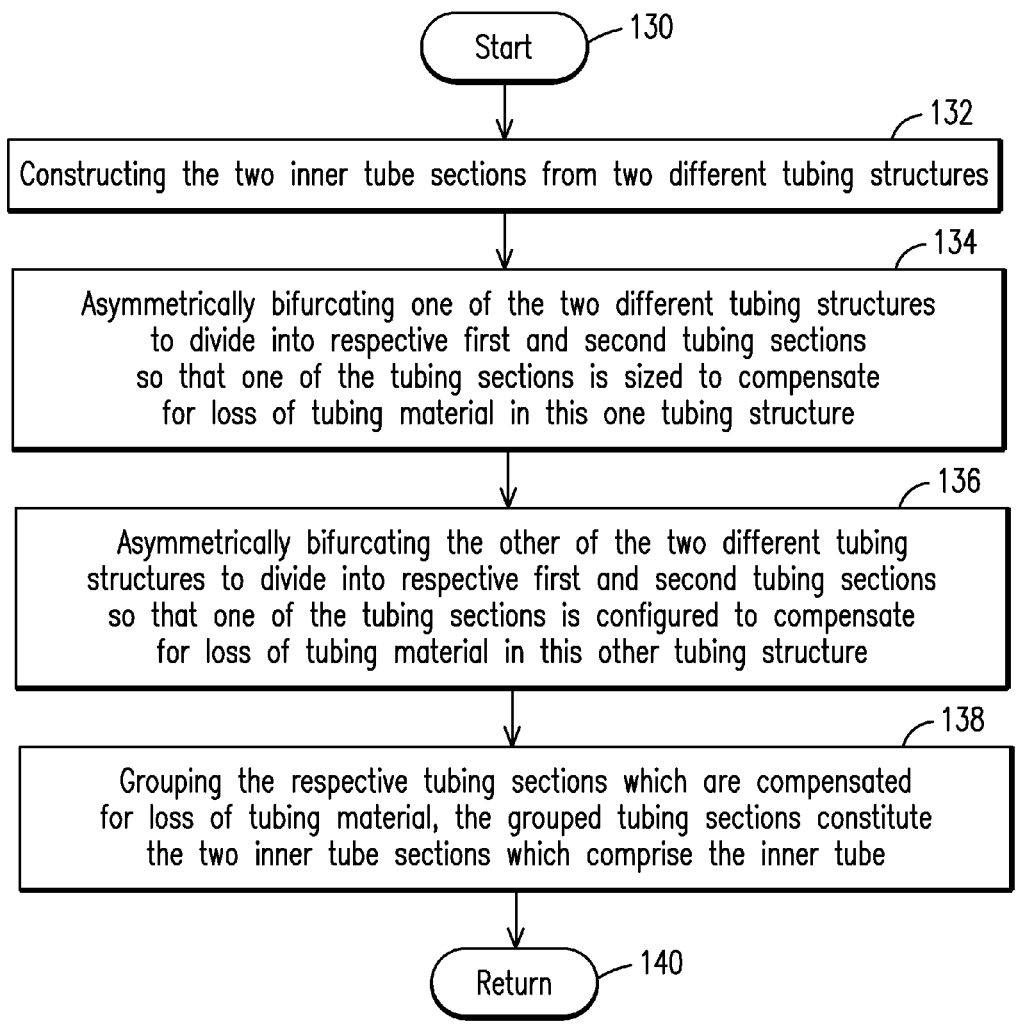

In one-limiting embodiment and referring to the flow chart shown in FIG. 8 (and the respective isometric views shown in FIG. 9), subsequent to a start step 130, step 132 allows constructing the two inner tube sections 34, 36 (FIG. 3) from two different tubing structures, such as tubing structures 150 and 152, as shown in FIG. 9. In one non-limiting embodiment, a constructing of a first the two inner tube sections may comprise asymmetrically bifurcating (step 134) along its longitudinal axis 151 one of the two different tubing structures (e.g., tubing structure 150 in FIG. 9) to divide into respective first and second tubing sections 154, 156. The asymmetrical bifurcating is arranged so that one of the first and second tubing sections (e.g., tubing section 154, labeled C1) is sized to compensate for loss of tubing material (conceptually represented by strip 158) due to the bifurcating of tubing structure 150. Asymmetrical bifurcating may be conceptualized as partitioning no longer intended to divide the tube into two equal size portions.

A constructing of a second of the two inner tube sections 34, 36 may comprise asymmetrically bifurcating along its longitudinal axis (represented by arrow 153) the other (e.g., tubing section 152) of the two different tubing structures to divide into respective tubing sections 160, 162. The asymmetrical bifurcating is selected so that one of the first and second tubing sections (e.g., tubing section 162, labeled C2) is configured to compensate for loss of tubing material (conceptually represented by strip 164) due to the bifurcating of tubing structure 152. Prior to a return step 140, step 138 allows grouping the respective tubing sections which are compensated for loss of tubing material (e.g., tubing sections labeled C1 and C2). The grouped tubing sections labeled C1 and C2 constitute the two inner tube sections 34, 36 for inner tube 30. In one non-limiting embodiment, the tubing sections 154 and 160, which are not compensated for loss of tubing material may be discarded.

While various embodiments of the present invention have been shown and described herein, it will be apparent that such embodiments are provided by way of example only. Numerous variations, changes and substitutions may be made without departing from the invention herein. Accordingly, it is intended that the invention be limited only by the spirit and scope of the appended claims.

The invention claimed is:

1. An optical probe comprising:
at least one optical element;
an inner tube housing the at least one optical element, wherein the inner tube
comprises at least two cooperating inner tube sections separable from one another along respective joint lines co-axially extending in a direction along a longitudinal axis over an entire longitudinal length of the inner tube; and
a light-redirecting element disposed at a distal end of the inner tube, wherein the light-redirecting element is supported at said distal end by an affixing structure not attached to an optically-working surface of the light-redirecting element, wherein the affixing structure comprises at least one protrusion from the inner tube sections having a support surface attached to a non-optically working surface of the light-redirecting element, wherein the optical probe is structured to be partially disposed within a path of hot-temperature combustion gases in a combustion turbine engine.

2. The optical probe of claim 1, further comprising means for removably affixing the at least two corresponding inner tube sections to one another.

3. The optical probe of claim 1, further comprising at least one affixing element to removably affix the at least two cooperating inner tube sections to one another, wherein the at least one affixing element is selected from the group consisting of a strap, a tack-weld, and a threaded affixing element.

4. The optical probe of claim 1, wherein the at least two cooperating inner tube sections of the inner tube define a hollowed interior having a varying diameter along the longitudinal axis.

5. The optical probe of claim 1, wherein the at least one optical element comprises a series of optical lenses stacked along the longitudinal axis of the inner tube.

6. The optical probe of claim 5, further comprising at least one optical spacer interposed between at least a pair of the optical lenses.

7. The optical probe of claim 1, wherein the inner tube comprises a stop formed on an outer surface thereof.

8. The optical probe of claim 1, wherein the inner tube comprises at least one alignment tab formed on an outer surface thereof.

9. The optical probe of claim 1, wherein the at least one protrusion is integrally constructed at the distal end of the inner tube.

10. The optical probe of claim 1, wherein the light-redirecting element is selected from the group consisting of a prism and a mirror.

11. The optical probe of claim 1, further comprising an outer tube housing the inner tube.

12. An optical probe comprising:
at least one optical element;
an inner tube housing the at least one optical element, wherein the inner tube comprises at least two cooperating inner tube sections separable from one another along a longitudinal axis of the inner tube; and
a light-redirecting element disposed at a distal end of the inner tube, wherein the light-redirecting element is supported at said distal end by an affixing structure not attached to an optically-working surface of the light-redirecting element, wherein the affixing structure comprises at least one protrusion from the inner tube sections having a support surface attached to a non-optically working surface of the light-redirecting element, further comprising adhesive between the support surface and the non-optically working surface of the light-redirecting element.

13. An optical probe comprising:
at least one optical element;
an inner tube housing the at least one optical element, wherein the inner tube comprises at least two cooperating inner tube sections separable from one another along a longitudinal axis of the inner tube; and
a light-redirecting element disposed at a distal end of the inner tube, wherein the light-redirecting element is supported at said distal end by an affixing structure not attached to an optically-working surface of the light-redirecting element, wherein the light-redirecting element comprises a prism, and further wherein the affixing structure comprises respective protrusions from the inner tube sections, each protrusion having a support surface attached to a corresponding lateral surface of the prism.

14. The optical probe of claim 13, further comprising adhesive disposed between the support surfaces and the lateral surfaces of the prism.

* * * * *